(12) United States Patent
Sahatjian et al.

(10) Patent No.: US 6,629,947 B1
(45) Date of Patent: *Oct. 7, 2003

(54) SYSTEMS AND METHODS FOR DELIVERING FLOWABLE SUBSTANCES FOR USE AS IMPLANTS AND SURGICAL SEALANTS

(75) Inventors: Ronald A. Sahatjian, Lexington, MA (US); Robert Boock, Minnetonka, MN (US)

(73) Assignee: Boston Scientific Corporation, Natick, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/330,175

(22) Filed: Jun. 11, 1999

Related U.S. Application Data (63) Continuation-in-part of application No. 08/919,107, filed on Aug. 28, 1997, now Pat. No. 6,139,620, which is a continuation-in-part of application No. 08/776,943, filed as application No. PCT/CH95/00184 on Aug. 16, 1995, now Pat. No. 6,296,632.

(51) Int. Cl.[7] ................................. A61F 13/20
(52) U.S. Cl. ..................... 604/13; 606/213; 604/11; 604/57; 604/502
(58) Field of Search .................. 606/1, 151, 200, 606/213; 604/890.1, 891.1, 1, 2, 11–18, 46, 500, 27, 502, 506, 507, 514, 518, 57, 59, 264

(56) References Cited

U.S. PATENT DOCUMENTS

| | | | |
|---|---|---|---|
| 2,524,195 A | 10/1950 | Hoover | |
| 3,431,907 A | 3/1969 | Lubet-Moncla | |
| 3,481,335 A | 12/1969 | Beutlich | |
| 3,527,225 A | * 9/1970 | Smith | 606/239 |
| 3,703,174 A | 11/1972 | Smith | |

(List continued on next page.)

FOREIGN PATENT DOCUMENTS

| | | |
|---|---|---|
| DE | 31 15763 | 11/1982 |
| EP | 0186632 | 7/1986 |
| EP | 0 424 068 A2 | 4/1991 |
| EP | 0621020 | 10/1994 |
| FR | 2696636 | 4/1994 |

(List continued on next page.)

OTHER PUBLICATIONS

Taki, K., "Possibility and Limit of Intravascular Surgery"; Medical Tribune, pp. 46–47, Oct. 1989, Nippon Accel Shubringer Shuppan, K.K.

(List continued on next page.)

*Primary Examiner*—Glenn K. Dawson
(74) *Attorney, Agent, or Firm*—Finnegan, Henderson, Farabow, Garrett & Dunner, L.L.P.

(57) ABSTRACT

A system for delivering a flowable substance capable of changing from liquid to solid for use as implants and surgical sealants includes a first reservoir containing a first flowable substance including a bulking agent, a second reservoir containing a second flowable substance including a reacting agent, and a cannula. A method of delivering flowable substance that changes from liquid to solid for use as implants and surgical sealants includes introducing a cannula having first and second lumens into the body, passing a flowable substance including a bulking agent through the first lumen, passing a second flowable substance including a reacting agent through the second lumen, mixing the first and second flowable substances in the cannula so that the bulking agent reacts with the reacting agent to form a flexible elongated fiber in the cannula, and moving the fiber through the opening in the cannula and into the body to form at least one of an implant and surgical seal.

39 Claims, 4 Drawing Sheets

U.S. PATENT DOCUMENTS

| | | |
|---|---|---|
| 3,826,256 A | 7/1974 | Smith |
| 3,906,550 A | 9/1975 | Rostoker et al. |
| 4,159,022 A | 6/1979 | Pevsner |
| 4,237,885 A | 12/1980 | Wong et al. |
| 4,402,308 A | 9/1983 | Scott |
| 4,512,338 A | 4/1985 | Balko et al. |
| 4,551,132 A | 11/1985 | Pasztor et al. |
| 4,712,553 A | 12/1987 | MacGregor |
| 4,820,267 A | 4/1989 | Harman |
| 4,820,767 A | 4/1989 | Wu |
| 4,840,622 A | 6/1989 | Hardy |
| 4,932,942 A | 6/1990 | Maslanka |
| 4,950,295 A | 8/1990 | Weigum et al. |
| 4,979,942 A | 12/1990 | Wolf et al. |
| 4,994,069 A | 2/1991 | Ritchart et al. |
| 5,021,059 A | 6/1991 | Kensey et al. |
| 5,057,606 A * | 10/1991 | Garbe .......... 536/54 |
| 5,074,840 A | 12/1991 | Yoon |
| 5,100,392 A | 3/1992 | Orth et al. |
| 5,211,627 A | 5/1993 | William |
| 5,230,853 A * | 7/1993 | Colegrove et al. .......... 264/186 |
| 5,250,071 A | 10/1993 | Palermo |
| 5,256,146 A | 10/1993 | Ensminger et al. |
| 5,263,927 A | 11/1993 | Shlain |
| 5,308,342 A | 5/1994 | Sepetka et al. |
| 5,318,524 A | 6/1994 | Morse et al. |
| 5,322,510 A | 6/1994 | Lindner et al. |
| 5,336,263 A | 8/1994 | Ersek et al. |
| 5,374,261 A | 12/1994 | Yoon |
| 5,376,118 A | 12/1994 | Kaplan et al. |
| RE34,866 E | 2/1995 | Kensey et al. |
| 5,443,454 A | 8/1995 | Tanabe et al. |
| 5,454,833 A | 10/1995 | Boussignac et al. |
| 5,514,158 A | 5/1996 | Kanesaka |
| 5,522,795 A | 6/1996 | Green et al. |
| 5,522,822 A | 6/1996 | Phelps et al. |
| 5,545,169 A | 8/1996 | Yarger |
| 5,571,189 A | 11/1996 | Kuslich |
| 5,575,815 A | 11/1996 | Slepian et al. |
| 5,591,224 A | 1/1997 | Schwartz et al. |
| 5,614,204 A | 3/1997 | Cochrum |
| 5,660,854 A | 8/1997 | Haynes et al. |
| 5,667,778 A | 9/1997 | Atala |
| 5,690,666 A | 11/1997 | Berenstein et al. |
| 5,746,747 A | 5/1998 | McKeating |
| 5,766,160 A | 6/1998 | Samson et al. |
| 5,814,022 A * | 9/1998 | Antanavich et al. ........ 604/191 |
| 5,836,970 A * | 11/1998 | Pandit .......... 606/213 |
| 5,911,717 A | 6/1999 | Jacobsen et al. |
| 5,935,437 A * | 8/1999 | Whitmore ............. 210/321.6 |
| 5,954,682 A | 9/1999 | Petrus |
| 6,139,520 A * | 10/2000 | McCrory et al. .......... 604/60 |
| 6,258,055 B1 * | 7/2001 | McCrory et al. .......... 604/60 |
| 6,296,632 B1 | 10/2001 | Lüscher et al. |
| 6,299,590 B1 | 10/2001 | Lüscher et al. |

FOREIGN PATENT DOCUMENTS

| | | |
|---|---|---|
| JP | 61-161220 | 7/1986 |
| JP | 2-280768 | 11/1990 |
| JP | 2-280769 | 11/1990 |
| JP | 2-280770 | 11/1990 |
| JP | 2-280771 | 11/1990 |
| JP | 4-20348 | 1/1992 |
| JP | 4-197359 | 7/1992 |
| JP | 5-208917 | 8/1993 |
| WO | WO 91/13592 | 9/1991 |
| WO | WO 93/00127 | 1/1993 |
| WO | 5-504695 | 7/1993 |
| WO | WO 94/16632 | 8/1994 |
| WO | WO 95/08291 | 3/1995 |
| WO | WO 96/04954 A1 | 2/1996 |
| WO | WO 96/04954 | 2/1996 |
| WO | WO 97/19643 | 6/1997 |

OTHER PUBLICATIONS

Bernatchez et al., "Biocompatibility of a New Semisolid Bioerodible Poly (ortho ester) Intended for the Ocular Delivery of 5–fluorouracil"; Journal of Biomedical Materials Research; vol. 28, No. 9, pp. 1037–1046, Sep., 1994.

Bernatchez et al., "Biotolerance of Semisolid Hydrophobic Biodegradable Poly (ortho ester) for Controlled Drug Delivery" Journal of Biomedical Materials Research; vol. 27, No. 5, pp. 677–681, May, 1993.

Rüfenacht, D.A. et al., "A Simple Propulsion–Chamber System for the 16 Gauge Approach"; Neuroradiology (1986) 28:355–358.

Marks, R., et al., "Principles of Weaving"; The Textile Institute Manchester, 1976, pp. 130–135.

Taki et al., "The Eleventh General Meeting of Japan Biomaterial Society Collection of Scripts for Presentation"; Oct. 1989, at Kyoto University, Chief of the 11th Meeting: Takao Yamamuro.

Ayumi, Igaku No. [SIC] "Embolization Technique of Cerebral Arterial Aneurysm Advantages and Disadvantages of Embolization Technique and Surgical Operation"; vol. 153, No. 11, p. 635, Jun. 1990, Ishiyaku Publishers, Inc.

Goto, K., et al., "A New Technique for Embolization of Cerebral Arteriovenous Malformations and Dural Arteriovenous Fistulae"; Neuroradiology (1991) 33 [Suppl]: 193–194.

Harper, Marion, et al., "Isobutyl 2–cyanoacrylate as an Osseous Adhesive in the Repair of Osteochrondral Fractures"; Journal of Biomedical Materials Research, vol. 17, pp. 167–177 (1983).

A. Polk et al., "Controlled Release of Albumin from Chitsan–Alginate Microcapsules," Journal of Pharmaceutical Sciences, vol. 83, No. 2 (Feb. 1994), pp. 178–185.

K. Kamath et al., "Biodegradable Hydrogels in Drug Delivery," Advanced Drug Delivery Reviews, 11 (1993), pp. 59–84.

Serbinenko, F.A., M.D. "Balloon Catheterization and Occlusion of Major Cerebral Vessels,"; J. Neurosurg, vol. 41, Aug. 1974, pp. 125–145.

Ayumi, Igaku, No. [SIC], "Situation of New Subspeciality of Neurosurgery"; vol. 154, No. 7, p. 432, Aug. 1990, Ishiyaku Publishers, Inc.

Goto, K., "Recent Advances and Future Problems of Interventional Neuroradiology"; Neurosurgeons 9:229–239, Sep. 1990.

* cited by examiner

SYSTEMS AND METHODS FOR DELIVERING FLOWABLE SUBSTANCES FOR USE AS IMPLANTS AND SURGICAL SEALANTS

This application is a continuation-in-part (CIP) of U.S. patent application Ser. No. 08/919,107, filed on Aug. 28, 1997 (now U.S. Pat. No. 6,139,620), which is a continuation-in-part of U.S. patent application Ser. No. 08/776,943, filed as a 371 of application Ser. No. PCT/CH95/00184 on Aug. 16, 1995 (now U.S. Pat. No. 6,296,632). The entire disclosures of U.S. application Ser. Nos. 08/919,107 and 08/776,943 are incorporated herein by reference.

BACKGROUND OF THE INVENTION

1. Field of the Invention

The present invention relates to systems and methods for a delivering flowable substance capable of changing from liquid to solid for use as implants and surgical sealants. More particularly, the present invention relates to systems and methods for forming a fiber from a plurality of flowable substances, including a bulking agent.

2. Description of Related Art

Implants are used for treating a variety of diseases occurring in parts of the body that are extremely difficult to access and/or require relatively non-intrusive treatment techniques. For example, intracranial aneurysms are extremely difficult to treat because they are often formed in hard to reach cerebral blood vessels. If left untreated, hemodynamic forces of normal pulsatile blood flow can rupture fragile tissue in the area of the aneurysm causing a stroke. Some other examples of diseases that may be treated with implants include tumors in areas such as the liver, uterine fibroids, Gastro-Esophageal Reflex Disorder, urinary incontinence, and abdominal aortic aneurysms.

In one type of implant treatment, metallic coils are implanted in the body of a patient in an attempt to occlude blood flow to an aneurysm or tumor. Metal coil systems, however, suffer from several shortcomings. For example, metal coil systems do not form a sealed embolic implant that is encapsulated by tissue. Forming an unsealed embolic implant may result in clot lysis (i.e., disintegration) and/or other types of re-canalization of the targeted vessel. This procedure is also time consuming because it often requires bi-plane X-rays after the placement of each coil and the procedurist normally needs to determine and select the proper size for the coils prior to implantation. Further, when used in the treatment of aneurysms, coils can compact over time because they only fill approximately 40% of the aneurysm volume.

Polyvinyl alcohol (PVA) sponges have also been used as an implant to treat aneurysms and other diseases. However, like the metallic coils described above, PVA sponges have proved to be procedurally difficult to use and have failed to consistently achieve the desired results.

Other embolic systems include the use of polymers in solution, which begin to solidify or precipitate when contacted with blood or other bodily fluids. Such systems, however, suffer from the problem of the polymer solution migrating into undesired parts of the body because of the time delay necessary to cause formation or precipitation of the solid polymer. Migration in these polymer solution systems is particularly problematic when the solution is injected into "high flow" areas, such as vascular systems. Fibers formed from polymer solution systems also tend to suffer from other problems, such as not embolizing well, being overly brittle, or not being biocompatible.

Attempts have also been made to create an implant with adhesives, such as fibrin glues and sealants. However, these materials are thrombogenic and an embolic implant created is only temporary because of lysis of the implant by the body.

In light of the foregoing, there is a need in the art for an improved system and method for delivering a flowable substance that changes from liquid to solid for use as implants and surgical sealants.

SUMMARY OF THE INVENTION

Accordingly, the present invention is directed to systems and methods that substantially obviate one or more of the limitations of the related art. To achieve these and other advantages and in accordance with the purpose of the invention, as embodied and broadly described herein, the invention includes a system for delivering a flowable substance capable of changing from liquid to solid for use as implants and surgical sealants. The system includes a first reservoir containing a first flowable substance including an bulking agent and a second reservoir containing a second flowable substance including a reacting agent. The system also includes a cannula including a first lumen in fluid communication with the first flowable substance in the first reservoir, a second lumen in fluid communication with the second flowable substance in the second reservoir, a distal end portion wherein the first and second lumens fluidly communicate with one another to mix the first and second flowable substances and thereby form a flexible continuous fiber, and an opening in the distal end portion allowing passage of the fiber out of the distal end portion of the cannula.

In another aspect, at least one of the two flowable substances further includes an additive. The additive includes at least one of a reinforcing agent for providing structural support to the fiber, an active ingredient for providing a treatment to the body, an imaging agent for imaging the fiber, and a bioadhesive agent for adhering the fiber to at least one of itself and body tissue, and wherein after the first and second flowable substances are mixed, the additive is distributed throughout the fiber.

In yet another aspect, the present invention includes a method of delivering a flowable substance that changes from liquid to solid for use as implants and surgical sealants. The method includes introducing a cannula having a first lumen, a second lumen, and an opening in a distal end portion of the cannula into the body. A first flowable substance including an bulking agent is passed through the first lumen and a second flowable substance including a reacting agent is passed through the second lumen. The method also includes mixing the first and second flowable substances in the cannula to form a flexible elongated fiber and moving the fiber through the opening in the cannula into the body to form at least one of an implant and a surgical seal in the body.

In an aspect of the invention, the bulking agent includes alginate, and the reacting agent includes calcium.

In a further aspect, a cutter is provided on the cannula to sever a portion of the fiber passing through the lumen and opening of the cannula.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention. In the drawings.

FIG. 4 is a view of a cutter for the cannulas shown in FIGS. 1–3 and 3a;

DESCRIPTION OF THE PREFERRED EMBODIMENTS

Reference will now be made in detail to the present preferred embodiments of the invention, examples of which are illustrated in the accompanying drawings. Wherever possible, the same reference numbers are used in the drawings and the description to refer to the same or like parts, and the same reference numerals with alphabetical suffixes are used to refer to similar parts.

Figure 1:
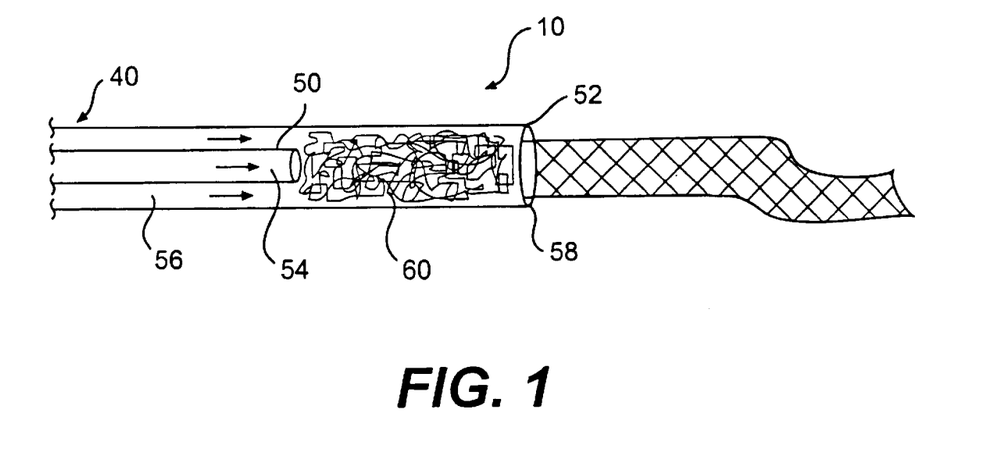
FIG. 1 is a view of a distal end portion of a cannula of a first embodiment of the invention.
Figure 2:
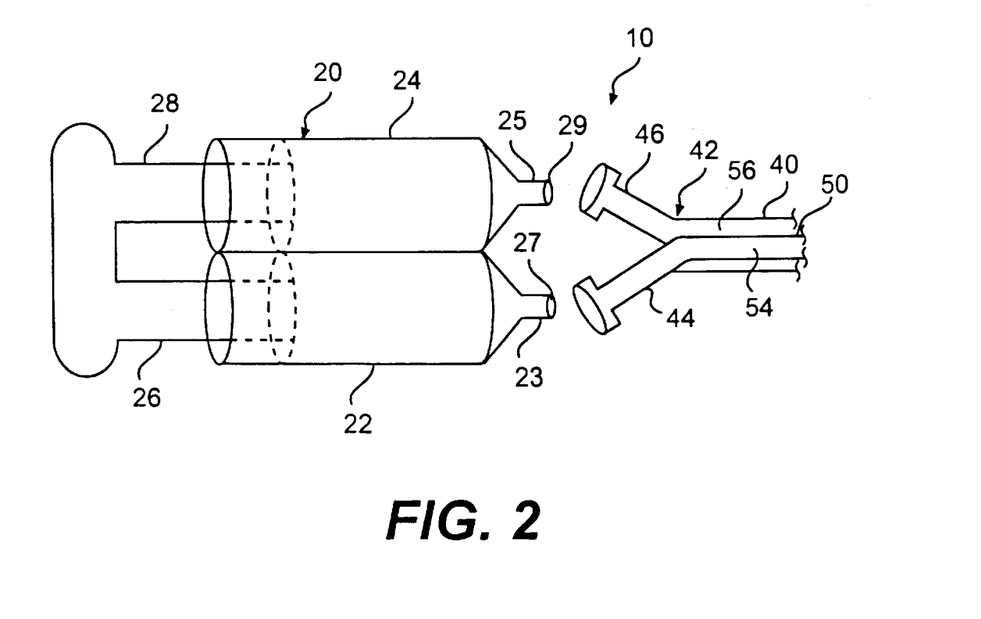
FIG. 2 is a view of a proximal end portion of the cannula of FIG. 1 and a dual barrel syringe for coupling to the cannula.

In accordance with the invention, there is provided an implant system including first and second reservoirs and a cannula having first and second lumens. FIGS. 1 and 2 respectively show distal and proximal end portions of a first embodiment of a system 10 in accordance with the present invention. As shown in FIG. 2, the system 10 includes a syringe 20 and a cannula 40 capable of being coupled together to introduce substances from the syringe 20 into the cannula 40.

The syringe 20 includes a first barrel 22 having a tip 23 formed with a discharge opening 27 and a second barrel 24 having a tip 25 formed with a discharge opening 29. The first and second barrels 22 and 24 respectively form a first reservoir containing a first flowable substance and a second reservoir containing a second flowable substance.

Preferably, the first flowable substance includes an bulking agent. The bulking agent is preferably chosen from water soluble polymers and polymer solutions including blood compatible solvent water mixtures, such as alcohol water and DMSO water solutions. More preferably, the bulking agent includes a water soluble polymer chosen from polyacids, cellulosic polymers, polylysine, collagen, gelatin, albumin, poly HEMA, PVP, chitosan, polymaleic anhydride, polyamide, polyacrylic acid, heparin, sodium carboxymethyl cellulose, polyacrylamide, polyvinylalcohol, polyethylene glycol, polyethers, functionalized polyethylene glycol derivatives, proteins, polysaccharide, and hydrogels (both cross-linkable and non-cross-linkable). Most preferably, the bulking agent includes a polysaccharide, such as alginate (i.e., sodium alginate, potassium alginate, barium alginate, magnesium alginate, or strontium alginate, or mixtures thereof), polyethylene oxide, carboxymethyl cellulose, or a carboxylic acid containing polysaccharide. The second flowable substance includes a reacting agent. The reacting agent is preferably chosen from ionic cross-linking agents, such as multi-valent ions, aldehyde cross-linkers, such as gluteraldehyde, divalent or trivalent ions, aziridine, D-glucono-gamma lactone, and/or isocyanates. More preferably, the reactant is a cross-linking agent chosen from calcium chloride, calcium gluconate, and calcium sulfate. Most preferably, the reactant includes an ionic cross-linking agent. When the bulking agent includes alginate, the reactant includes polyvalent cations, such as divalent cations. For example, the bulking agent of the first flowable substance is preferably a liquid including sodium alginate, and the second flowable substance is preferably a liquid solution including calcium, such as a liquid solution including calcium chloride, calcium gluconate, calcium sulfate, or mixtures thereof.

Preferably, at least one of the two flowable substances includes an additive. The additive preferably includes at least one of a reinforcing agent for providing structural support to the fiber, a bioadhesive agent for adhering the fiber to at least one of itself and body tissue, an active ingredient for providing a treatment to the body, and an imaging agent for imaging the fiber. After the two flowable substances are mixed, the additive is preferably distributed throughout the fiber.

The first flowable substance preferably includes the reinforcing agent for providing structural support to the fiber. Preferably, the reinforcing agent includes particulate material including a plurality of particles formed of at least one of metal, glass, and polymer, the particles being in the shape of at least one of spheres and needles. The particulate material is preferably DEAE Dextran. In the alternative, the reinforcing agent is chosen from zirconium oxide, PVA, PMMA, and other agents having microspheres.

The first flowable substance preferably also includes the bioadhesive agent for adhering the fiber to at least one of itself and body tissue. The bioadhesive agent is preferably chosen from cyanoacrylate, polylysine, chitosan, polyethylene oxide, polypropylene oxide, cellulose derivatives, carboxy-methyl cellulose, polyethers, polysaccharides, mucopolysaccharides, such as hylauronic acid, fatty acid esters, Pluronics, polyacids cellulosic polymers, collagen, gelatin, poly HEMA, PVP, polymaleick anhydride, polyamide, polyacrylarhide, polyvinylalcohol, and polyethylene glycol.

In a preferred embodiment, one of the flowable substances also includes an active ingredient for providing a treatment to the body. For example, the first flowable substance may include one or more active ingredients chosen from drugs, radioactive material that emits radiation, and growth enhancers. The drugs are preferably chosen from alcohol, anti-platelet drugs, anti-coagulant drugs, thrombogenic drugs, such as thrombin, anti-thrombogenic drugs, angiogenic drugs, anti-angiogenic drugs, and thrombolytic agents. In one embodiment, the drug is incorporated into microspheres to release the drug over a period of time. In an alternate embodiment, the first flowable substance includes radioactive particulate material that emits radiation and acts as a reinforcing agent. The growth enhancers are preferably chosen from VEGF, alpha or beta FGF, platelet derived growth factors, autologous cells, and nucleic acid that encodes a therapeutic protein, such as VEGF. For example, the bulking agent of the first flowable substance may include autologous cells that cause growth to occur or muscle cells that proliferate to provide bulking.

In another embodiment, the additive includes an imaging agent for imaging the fiber. The imaging agent is preferably chosen from radiopaque materials, such as tantalum, tungsten, platinum, gold, barium sulfate, and titanium dioxide, pigments, such as water soluble dyes, and MRI compatible enhancing agents.

As described below, when the bulking agent includes a polysaccharide and the reactant includes a cross-linking agent, the bulking agent and the reacting agent form a cross-linked polysaccharide fiber when they are mixed in the cannula 40. The first and second barrels 22 and 24 are preferably separate from one another to prevent this cross-linking from taking place in the syringe 20.

The syringe 20 also includes a first plunger 26 movable in the first barrel 22 and a second plunger 28 movable in the second barrel 24. Preferably, the first and second plungers 26 and 28 are coupled together so that they move together in the respective barrels 22 and 24 to eject the first and second liquids simultaneously from the discharge openings 27 and 29. As compared to separate plunger arrangements, the coupled first and second plungers 26 and 28 make it easier for a user to eject the first and second liquids at constant rates to form a more consistent cross-linked fiber.

As shown in FIG. 2, the proximal end portion of the cannula 40 includes an adapter 42 having first and second branches 44 and 46 capable of being coupled directly to the respective tips 23 and 25. Although the first and second branches 44 and 46 are preferably coupled directly to the tips 23 and 25, other coupling arrangements are possible. For example, separate lengths of flexible tubing could be provided to couple the tips 23 and 25 and the branches 44 and 46 fluidly together. In addition, the first and second branches 44 and 46 could be located at different locations on the cannula 40 without both being on the same adapter 42.

Preferably, the cannula 40 is a catheter having sufficient flexibility to allow for insertion into predetermined areas in a body. For example, the cannula 40 could be a flexible catheter, such as a micro catheter sufficiently flexible to be inserted into the cranial area to treat an aneurysm. In addition, the cannula 40 could be an endoscopic device, needle, or any other type of medical device having a generally tubular shape. Although the cannula 40 is preferably formed of a polymer, other materials, such as metal, can be used. To allow for imaging in the body, the cannula 40 preferably includes a portion or portions including radiopaque material.

As shown in FIG. 1, the cannula 40 includes a first tubular portion 50, a second tubular portion 52, and an opening 58 formed in the distal end of the cannula 40. The first tubular portion 50 is positioned coaxially within the second tubular portion 52 to form a first lumen 54 in the first tubular portion 50, and a second lumen 56 between an outer surface of the first tubular portion 50 and an inner surface of the second tubular portion 52. When the syringe 20 shown in FIG. 2 is coupled to the adapter 42 on the cannula 40, the first lumen 54 is placed in fluid communication with the first flowable substance in the first barrel 22, and the second lumen 56 is placed in fluid communication with the second flowable substance in the second barrel 24.

The first lumen 54 extends from the first branch 44 shown in FIG. 2 to its distal end shown in FIG. 1, and the second lumen 56 extends from the second branch 46 shown in FIG. 2 to its distal end shown in FIG. 1. Although the first and second lumens 54 and 56 are coaxially arranged and formed by the first and second tubular portions 50 and 52, other configurations are possible. For example, the first and second lumens could be adjacent lumens having independent axes and feeding into a single lumen segment (mixing chamber) at the distal tip portion of the catheter. Additionally, one of ordinary skill in the art will recognize that the invention covers a configuration having the tubular portions 50, 52 coaxial to each other with the second lumen being located in the first tubular portion 50 and the first lumen being located between and an outer surface of the first tubular portion 50 and an inner surface of the second tubular portion 52.

The distal end of the second tubular portion 52 extends further in the distal direction than the distal end of the first tubular portion 50. This staggered end relationship of the tubular portions 50 and 52 forms a mixing chamber 60 in the distal end portion of the cannula 40 between the first tubular portion 50 and the opening 58. Preferably, the segment of the outer tubular portion 52 that defines the mixing chamber 60 is configured like a microcatheter and is reinforced with a wire or fiber braid so that the catheter segment defining the mixing chamber 60 has the flexibility of a soft-tip microcatheter, while being rigid enough to allow formation of the fiber. The length of the mixing chamber 60 is preferably designed to have a length that allows the end segment of tubular portion 52 to be soft enough to prevent trauma to blood vessels, while optimizing strength and imaging of the fiber. The first and second lumens 54 and 56 communicate with one another in the mixing chamber 60. As the first and second flowable substances flow from the first and second lumens 54 and 56 to the mixing chamber 60, these flowable substances mix and form the fiber in the mixing chamber 60. The resulting fiber is flexible and has a diameter substantially the same as that of the inner surface of the second tubular portion 52. After the fiber is formed, it is extruded from the cannula 40 via the opening 58.

Preferably, the first flowable substance contained in the first barrel 22 of the syringe 20 is a solution including a polysaccharide, such as sodium alginate, and the second flowable substance contained in the second barrel 24 of the syringe 20 is a solution including an ionic cross-linking agent, such as calcium (i.e. calcium chloride) or some other cross-linking agent having divalent and trivalent ions. In the alternative, the first flowable substance is a solution including an ionic cross-linking agent and the second flowable substance includes a polysaccharide. For example, when sodium alginate and calcium chloride combine in the mixing chamber 60, the divalent cations (calcium ions) replace the sodium ions to form a cross-linked, hydrogel, alginate fiber. Because the resulting cross-linked alginate fiber is a hydrogel, it is possible to capture certain contrast substances into the hydrogel to make the fiber visible in MRI, CT, and fluoroscopy.

For example, radiopaque substances, such as tantalum, tungsten, barium sulfate, and/or titanium dioxide can be added to the first flowable substance and/or the second flowable substance to make the formed fiber radiopaque. Barium, which is a divalent cation, can be used to cross link with the polysaccharide and make it radiopaque. Certain solutions of iodine and/or gadolinium can also be solubilized in the liquid including polysaccharide prior to cross-linking and may remain trapped within the hydrogel after cross-linking, making it visible in certain imaging modalities. In particular, gadopentetate dimeglumine and/or iothalamate meglumine, which are water soluble salts used as contrast agents, can be combined with the polysaccharide to produce a hydrogel visible in both MRI and x-ray modalities (fluoroscopy, CT, DSA).

Certain drugs can also be added to the first and second flowable substances prior to forming the fiber so that the drugs are captured in the fiber as it forms in the mixing chamber 60. After implantation of the fiber in the body, the drugs are preferably released over time to provide particular treatments. For example, alcohol or cyanoacrylate could be added to the first and/or second flowable substance to provide a fiber capable of treating an arteriovenous malformation (AVM)—an abnormal network of vessel connections between an artery and vein. In addition, thrombogenic substances could be added to one of the flowable substances to form a fiber capable of inducing thrombosis in an aneurysm cavity.

In another embodiment, radioactive materials that emit radiation are added to at least one of the first and second flowable substances. Fibers including radioactive materials can be used to treat diseases, such as arteriosclerosis and restenosis.

A precipitating material can also be added to the first flowable substance and/or the second flowable substance prior to forming the fiber. The precipitating material precipitates and forms a matrix as the fiber is formed. This matrix preferably holds portions of the fiber together to stabilize the implant structure formed by the fiber and to prevent fiber migration in the body. For example, polyvinyl alcohol, sucrose acetate isobuty rate, or cellulose acetate could be added to the first flowable substances and/or the second flowable substance to form the matrix. The matrix may be desired when using the fiber to pack a cavity, such as an aneurysm sac.

Alternatively, an adhesive material, such as cyanoacrylate, polylysine, chitosan, polyethylene oxide, polypropylene oxide, cellulose derivatives, carboxy-methyl cellulose, polyethers, polysaccharides, mucopolysaccharides, such as hylauronic acid, fatty acid esters, Pluronics, polyacids cellulosic polymers, collagen, gelatin, poly HEMA, PVP, polymaleic anhydride, polyamide, polyacrylamide, polyvinylalcohol, and polyethylene glycol could be added to the first flowable substance and/or second flowable substance so that portions of the fiber adhere to one another and/or body tissue after implant formation. Adding a bioadhesive stabilizes the implant and prevents fiber migration, especially when packing a cavity.

When the first flowable substance includes alginate, the first flowable substance and/or the second flowable substance also may include a different polymer, such as polylysine and/or hylauronic acid. Polylysine and hylauronic acid form an electrostatic interaction with alginate. For example, when a cross-linked alginate fiber is formed, alginate and polylysine form a polymer entanglement to provide structural integrity.

Figure 3:
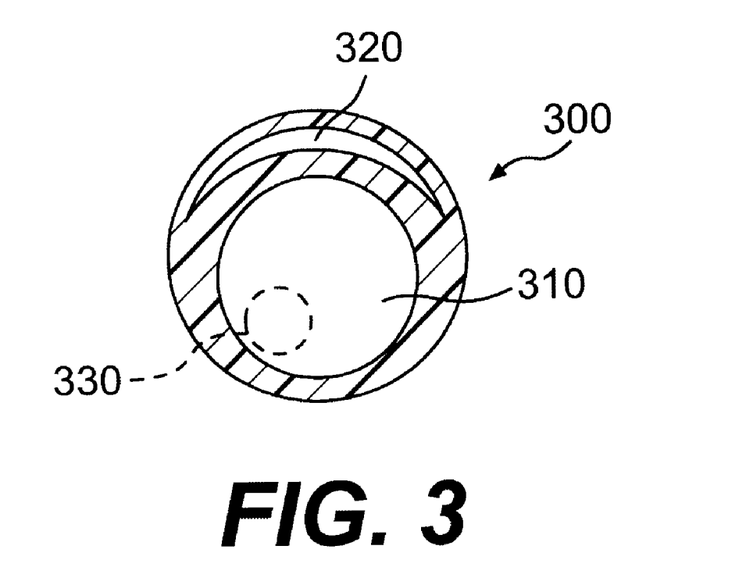
FIG. 3 is a cross-sectional view of an alternate embodiment of a cannula.
Figure 3A:
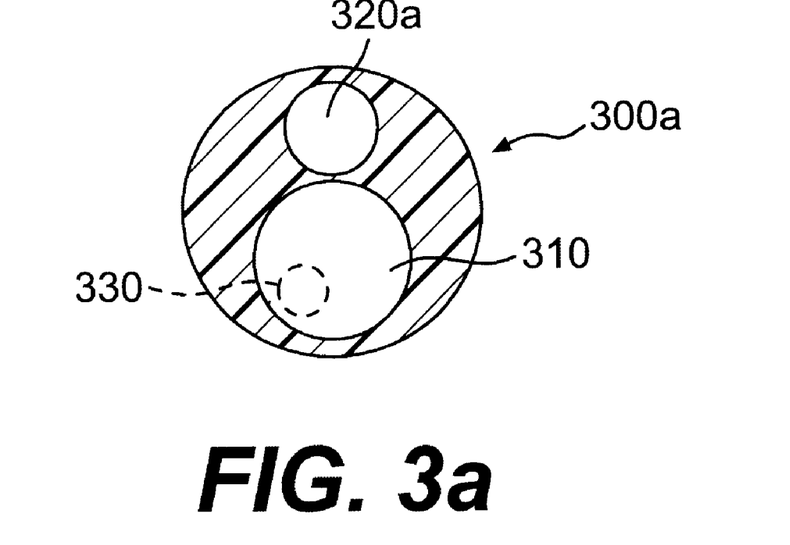
FIG. 3a is a cross-sectional view of another embodiment of a cannula.

FIG. 3 shows a cross-sectional view of an alternate embodiment of the invention including a cannula 300. Similar to the cannula 40 of FIGS. 1 and 2, the cannula 300 includes a first lumen 310 and a second lumen 320. The first lumen 310 has a circular cross-section and the second lumen 320 has a crescent-shaped cross-section. Unlike the cannula 40 of FIGS. 1 and 2, however, the lumens 310, 320 are not coaxial to each other. Rather, the lumens 310, 320 are positioned adjacent to one another so that a concave side of the second lumen 320 is facing the first lumen 310. Although FIG. 3 shows the second lumen as having a crescent-shaped cross-section, the second lumen may have other cross-sectional shapes as well. For example, as shown in FIG. 3a, a second lumen 320a is circular in cross-section. The second lumen may also have an oval-shaped cross-section. The lumens 310, 320 are both connected to a mixing chamber (not shown), similar to the mixing chamber 60 shown in FIG. 1, where the lumens 310, 320 fluidly communicate with one another. Preferably, this mixing chamber has a length selected to optimize fiber strength and to facilitate severing of the fiber by stopping flow of the bulking agent and by flushing the mixing chamber with the reacting agent. The mixing chamber preferably has an axial length of approximately 10 cm or less. More preferably, the axial length is approximately 2 cm or less. The cannula 300 is preferably used with a dual-barrel syringe similar to the syringe 20 shown in FIG. 2.

A guide wire 330 is provided in the first lumen 310 to guide the cannula 300 into a body. The configuration of the cannula 300 is preferable to the coaxial configuration shown in FIGS. 1 and 2, since the cannula 300 provides a more compact profile. Preferably, the guide wire 330 is removed from the first lumen 310 after the cannula 300 is positioned in the body. In an alternative embodiment, the lumens 310, 320 are configured so that the guide wire 330 can be provided in either of the lumens 310, 320. Preferably, after initial positioning of the cannula 300 in the body, the guide wire 330 can be re-introduced into the cannula 300 through the second lumen 320 to reposition the cannula 300 during a procedure.

Figure 4:
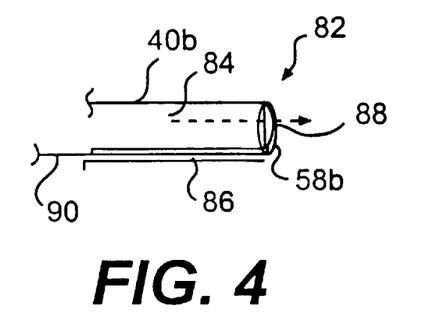

FIG. 4 shows an embodiment of the invention including a cutter 82 for severing the fiber. The cutter 82 is on a distal end portion of a cannula 40b including a primary lumen 84, an auxiliary lumen 86, and a distal opening 58b. With the exception of the auxiliary lumen 86, the cannula 40b is preferably constructed like the cannula 40 shown in FIGS. 1 and 2, the cannula 300 of FIG. 3, or one of the cannulas disclosed in U.S. patent application Ser. No. 08/776,943, the disclosure of which is incorporated herein by reference.

The cutter 82 is preferably a strand of wire having a loop shaped portion 88 and a substantially straight actuator portion 90 extending from the loop shaped portion 88. The loop shaped portion 88 is positioned in the distal end portion of the cannula 40b along an inner surface of the lumen 84 so that the loop shaped portion 88 surrounds the fiber when the fiber passes through the lumen 84 and the opening 58b. The actuator portion 90 extends through the auxiliary lumen 86 to a proximal end portion of the cannula 40b. Alternatively, the actuator portion 90 extends through the primary lumen 84 or on the outside of the cannula 40b when the cannula does not have an auxiliary lumen.

Figure 5A:
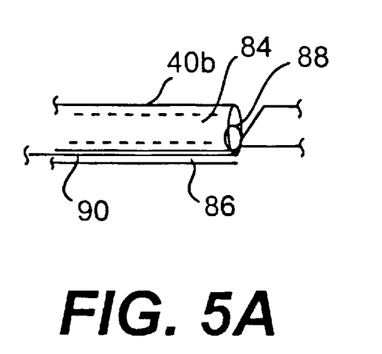
FIGS. 5a and 5b are views showing how the cutter of FIG. 4 severs a fiber.
Figure 5B:
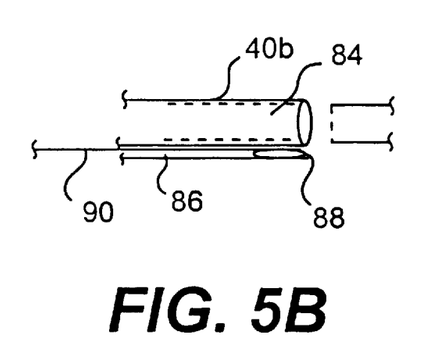

FIGS. 5a and 5b show how the cutter 82 severs the fiber after a desired length of fiber has passed through the opening 58b. As shown in FIG. 5a, when the actuator 90 is moved in the proximal direction with respect to the cannula 40b, the loop shaped portion 88 passes across the lumen 84 and through the fiber to begin severing the fiber. Continued pulling of the actuator 88 completely severs the fiber, as shown in FIG. 5b, and places the loop shaped portion in the auxiliary lumen 86.

Figure 6:
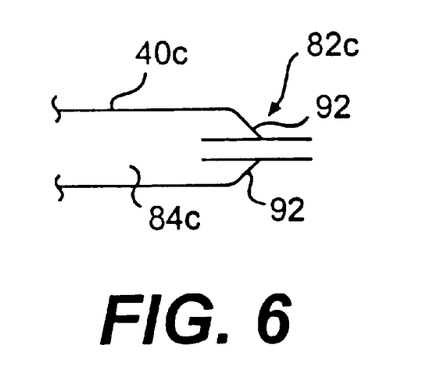
FIG. 6 is a view of an alternate embodiment of a cutter for the cannulas shown in FIGS. 1–3.
Figure 7:
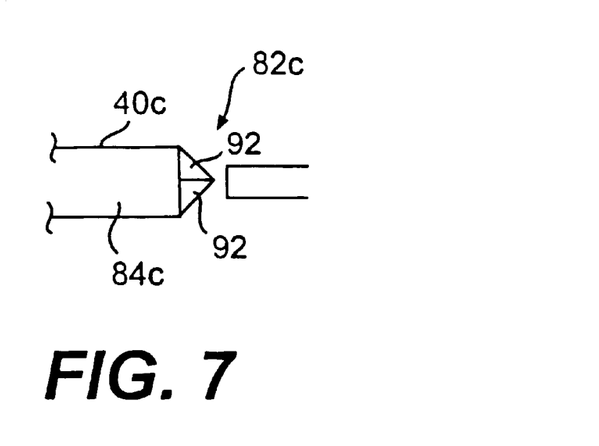
FIG. 7 is a view of the cutter of FIG. 6 after the cutter severs a fiber.
Figure 8:
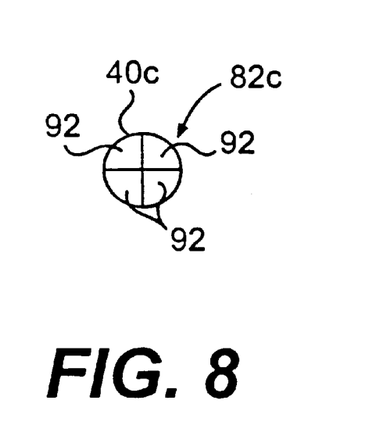
FIG. 8 is a distal end view of the cutter of FIG. 7.

FIGS. 6, 7, and 8 show an alternate embodiment of a cutter 82c for severing the fiber. The cutter 82c is mounted on a cannula 40c constructed like the cannula 40 shown in FIGS. 1 and 2, the cannula 300 shown in FIG. 3, or one of the cannulas disclosed in above-mentioned U.S. patent application Ser. No. 08/776,943. The cannula 40c includes a lumen 84c allowing for passage of the fiber therethrough.

As shown in the distal end view of FIG. 8, the cutter 82c includes a plurality of resilient flaps or leaflets 92 biased toward one another to form a compliant slit valve. The leaflets 92 move away from one another in response to movement of the fiber against an inner surface of the leaflets 92 and increased fluid pressure in the lumen 84c generated by the syringe 20 shown in FIG. 2. As shown in FIG. 6, sufficient pressure of the fiber and fluid in the lumen 84c forces the leaflets 92 away from one another to create an opening having a size sufficient to allow for passage of the fiber from the distal end portion of the cannula 40c. When this pressure is reduced, the leaflets 92 resiliently close on the fiber to sever or pinch off the fiber, as shown in FIG. 7.

Other types of cutters may also be provided for severing the fiber. For example, an alternate embodiment of a cutter includes an electrode attached to the cannula that becomes heated when provided with an electric current to sever the fiber. In one embodiment, the electrode is a radiopaque marker electrically connected to a RF source and grounded to a patient. The fiber is severed by signaling the RF source to provide electric current to the electrode and thereby heat the electrode. Further embodiments of cutters for severing a fiber include a fiber optic tip on the cannula that provides laser energy sufficient to sever the fiber formed by the cannula, as well as other types of heat sources for severing the fiber with heat.

In an alternate embodiment, the adapter 42, shown in FIG. 2, is configured to allow an operator to move the first tubular portion 50, shown in FIGS. 1 and 2, axially in the second tubular portion 52. With such an arrangement, the first tubular portion 50 may be moved axially toward the distal opening 58 to push the formed fiber from the mixing chamber 60 and thereby separate the fiber from the cannula 40. This arrangement also allows the procedurist to change the length of the mixing chamber 60 to optimize the strength of the fiber. In a preferred embodiment, the mixing chamber 60 has an axial length of approximately 2 cm or less.

Methods of forming an implant in a body are discussed below with reference to FIGS. 1–2, 5a, 5b, and 6–8. Although the invention is described in connection with the structure shown in these figures, it should be understood that the invention in its broadest sense is not so limited.

Initially, the distal end portion of the cannula 40 shown in FIGS. 1 and 2 is inserted in the body of a patient and the distal end is guided to a site where the implant is to be formed. To facilitate the insertion, a guide wire is inserted in the first lumen 54 and the cannula 40 is moved over the guide wire. In an alternate embodiment, the guide wire could be inserted into the second lumen 56 to position the cannula 40. In addition, the movement of the cannula 40 can be monitored fluoroscopically.

When the cannula is properly positioned, the guide wire is preferably removed from the first lumen 54 (or second lumen 56) and the syringe 20 is coupled to the adapter 42. Then, the plungers 26 and 28 are moved simultaneously in the barrels 22 and 24 to eject the first and second flowable substances respectively through the lumens 54 and 56 and into the mixing chamber 60. In the mixing chamber 60, the bulking agent, e.g., alginate, and the reactant, e.g., a cross-linking agent, react to form a cross-linked polysaccharide fiber in the mixing chamber 60. For example, when the first flowable substance includes sodium alginate and the second flowable substance includes calcium chloride, a cross-linked alginate fiber forms in the mixing chamber 60. The resulting fiber is flexible and has an outer surface matching the inner surface of the second tubular portion 52. As the fiber is formed, the fiber is ejected from the cannula 40 via the opening 58.

Since the fiber is formed inside the cannula 40, the fiber is in one continuous piece as it is injected into a vessel or a cavity. If the injection of both the first and second liquids continue, the fiber continues to form as one piece and is extruded out of the end of the cannula 40. This allows the fiber to stay together and reduces the chance of unintended embolization. As the fiber passes from the cannula 40, the fiber contacts tissue and curls up on itself inside the cavity it is filling to form a ball or nest shaped implant structure. Preferably, the consistency of the cross-linked alginate fiber is soft enough to allow dense packing inside the cavity.

As mentioned above, an agent, such as tantalum, tungsten, barium sulfate, and/or titanium dioxide can be added to at least one of the first and second liquids to make the resulting fiber radiopaque. As the fiber is formed, a procedurist can monitor the formation and implantation of the fiber via imaging equipment.

The fiber can be delivered via the cannula 40, shown in FIGS. 1 and 2, into a blood vessel to occlude the vessel partially or completely. For example, the fiber could be delivered into a blood vessel leading to an aneurysm to disrupt blood flow to the aneurysm by occluding the vessel. The fiber could also be used to treat an AVM by delivering the fiber into a vessel leading to the AVM to disrupt blood flow to the AVM. In addition, the fiber could be delivered to a blood vessel leading to a tumor to disrupt blood flow to the tumor, for example, a tumor in the liver. In the alternative, the fiber could be delivered to a blood vessel leading to a uterine fibroid to disrupt blood flow to the fibroid. The fiber can further be delivered to venous occlusions in the peripheral vascular system.

In a preferred method, the distal end of the cannula 40, shown in FIGS. 1 and 2, is placed in an aneurysm and the cross-linked fiber is ejected to fill the sac or cavity of the aneurysm at least partially. When the fiber contacts tissue in the cavity it curls back on itself making a ball or nest of fiber that provides packing in the cavity. This ball or nest of fiber is able to fill an irregularly shaped sac completely. When the fiber includes alginate, the alginate material provides a biocompatible surface at the aneurysm neck for endothelial cell growth. Preferably, the fiber also includes a growth enhancer. In addition, the fiber mass disrupts blood flow to the aneurysm and protects the fragile aneurysm wall from rupturing since it is no longer exposed to the hemodynamic forces of the normal pulsatile blood flow.

Preferably, the first flowable substance and/or the second flowable substance include a precipitating material or an adhesive agent when the fiber is delivered to fill an aneurysm sac or cavity. The precipitating material forms a matrix for holding the fiber implant together, and the adhesive adheres portions of the fiber to one another and to the walls of the aneurysm cavity. This maintains the implant in the sac and prevents fiber migration in the body.

Because the fiber is flexible, the nest or ball of fiber is more dense than a rigid metal coil and fills a higher percentage of volume of the blood vessel or the aneurysm cavity. As mentioned above, a thrombogenic substance can be added to one of the first and second liquids. When a fiber having this substance is implanted in an aneurysm cavity, it releases the thrombogenic substance to induce thrombosis in the cavity.

As compared to some gels used to fill aneurysms, it is easier to control the volume of the fiber. In addition, the fiber fills the cavity more completely to minimize leakage and may take up more volume than beads of gel. Also, the fiber preferably does not embolize rapidly.

In a further method, the fiber implant is used to treat an abdominal aortic aneurysm by injecting the fiber in an aneurysm in a blood vessel between the aneurysm and a vascular stent graft provided therein to fill the aneurysm and to seal an opening between the vascular stent graft and the aneurysm.

In another method, the distal end of the cannula 40, shown in FIGS. 1 and 2, is inserted into the body and used to deliver the fiber into soft tissue to provide embolization of the soft tissue. For example, the fiber could be delivered into the submucosa proximal to the urethral sphincter to provide bulking for the treatment of bladder incontinence. In the alternative, the fiber could be delivered at a junction between the esophagus and the stomach to aid in the treatment of Gastro-Esophageal Reflex Disorder.

The dual barrel syringe 20 shown in FIG. 2 allows for constant infusion of both the first flowable substance and the second flowable substance to the mixing chamber 60 shown in FIG. 1. Because the fiber is formed in the mixing chamber 60 of the cannula 20 itself, there is no need to manufacture the fiber separately, install it in a delivery device, and use a carrier fluid.

When using the system 10 shown in FIGS. 1 and 2, the length of fiber filling the body cavity does not need to be pre-determined. The fiber continues to form as long as the first and second flowable substances are injected. Preferably, the implanted portion of the fiber can be severed from the portion of fiber in the mixing chamber 60 by stopping flow of the bulking agent and flushing the mixing chamber 60 with the reacting agent. In an alternate embodiment, the cutter 82 shown in FIGS. 4, 5a, and 5b or the cutter 82c shown in FIGS. 6–8 can be used to sever the implanted portion of the fiber from the portion of fiber residing in the mixing chamber 60. In still another embodiment, when the first tubular portion 50, shown in FIGS. 1 and 2, is axially movable in the second tubular portion 52, the first tubular portion 50 may be moved axially toward the distal opening 58 to push the formed fiber from the mixing chamber 60 and thereby separate the fiber from the cannula 40.

It will be apparent to those skilled in the art that various modifications and variations can be made to the structure and methodology of the present invention without departing from the scope or spirit of the invention. In view of the foregoing, it is intended that the present invention covers modifications and variations of this invention, provided that they fall within the scope of the following claims and their equivalents.

What is claimed is:

1. A system for delivering flowable substance capable of changing from liquid to solid for use as implants and surgical sealants, the system comprising:
    a first reservoir containing a first flowable substance including an bulking agent;
    a second reservoir containing a second flowable substance including a reacting agent; and
    a cannula including
        a first lumen in fluid communication with the first flowable substance in the first reservoir,
        a second lumen in fluid communication with the second flowable substance in the second reservoir,
        a distal end portion wherein the first and second lumens fluidly communicate with one another, and
        an opening in the distal end portion allowing passage out of the distal end portion of the cannula,
    wherein the cannula and the first and second flowable substances are configured so that the first and second flowable substances mix and form a fiber in the distal end portion of the cannula, and
    wherein the opening allows passage of the fiber out of the distal end portion of the cannula.

2. The system of claim 1, wherein the distal end portion of the cannula includes a cutter for severing the fiber.

3. The system of claim 1, wherein the distal end portion of the cannula includes flexible material so that the cannula may be inserted into a body without causing trauma to the body.

4. The system of claim 3, wherein the cannula includes a reinforced section having at least one of a wire and a fiber braid.

5. The system of claim 1, further comprising a syringe having a first barrel forming the first reservoir and a second barrel forming the second reservoir.

6. The system of claim 1, wherein the first lumen is positioned adjacent to the second lumen.

7. The system of claim 6, further comprising a guide wire in at least one of the first and second lumens.

8. The system of claim 7, wherein the cannula is configured to allow removal of the guide wire from said at least one of the first and second lumens prior to the mixing of the first and second flowable substances and to allow reintroduction of the guide wire into the second lumen to position the cannula during a procedure.

9. The system of claim 6, wherein the distal end portion of the cannula defines a mixing chamber for mixing the first flowable substance with the second flowable substance, the length of the mixing chamber being sized to optimize fiber strength and to allow severing of a portion of the fiber in the body from a portion of the fiber in the mixing chamber by stopping flow of the first flowable substance and flushing the mixing chamber with the second flowable substance.

10. The system of claim 6, wherein the shape of the cross-section of the first lumen is circular and the shape of the cross-section of the second lumen is chosen from circular, oval, and cresent.

11. The system of claim 1, wherein the first lumen and the second lumen are coaxial.

12. The system of claim 11, wherein the cannula comprises a first tubular portion and a second tubular portion, the first lumen being between the first and second tubular portions and the second lumen being in the second tubular portion, the distal end portion being defined by a distal end segment of the first tubular portion.

13. The system of claim 12, wherein the distal end portion defines a mixing chamber for mixing the first flowable substance with the second flowable substance, the length of the mixing chamber being sized to optimize fiber strength and to allow severing of the fiber by stopping flow of the first flowable substance and flushing the mixing chamber with the second flowable substance.

14. The system of claim 11, wherein the cannula comprises a first tubular portion and a second tubular portion, the first lumen being in the second tubular portion and the second lumen being between the first and second tubular portions, the distal end portion being defined by a distal end segment of the first tubular portion.

15. The system of claim 14, wherein the distal end portion defines a mixing chamber for mixing the first flowable substance with the second flowable substance, the length of the mixing chamber being sufficient to optimize fiber strength and to allow quick severing of the fiber by stopping flow of the second flowable substance.

16. The system of claim 1, wherein at least one of the two flowable substances further includes an additive, the additive including at least one of a reinforcing agent for providing structural support to the fiber, an active ingredient for providing a treatment to the body, an imaging agent for imaging the fiber, and a bioadhesive agent for adhering the fiber to at least one of itself and body tissue, and wherein after the first and second flowable substances are mixed, the additive is distributed throughout the fiber.

17. The system of claim 16, wherein the additive includes at least the reinforcing agent.

18. The system of claim 17, wherein the reinforcing agent includes particulate material.

19. The system of claim 18, wherein the particulate material includes a plurality of particles formed of at least one of metal, glass, and polymer, the particles being in the shape of at least one of spheres and needles.

20. The system of claim 19, wherein the plurality of particles include radioactive material that emits radiation.

21. The system of claim 18, wherein the particulate material is chosen from DEAE Dextran, zirconium oxide, PVA, and PMMA.

22. The system of claim 16, wherein the additive includes at least the active ingredient.

23. The system of claim 22, wherein the active ingredient includes at least one drug.

24. The system of claim 13, wherein the at least one drug is chosen from alcohol, anti-platelet drugs, anti-coagulant drugs, thrombogenic drugs, thrombin, anti-thrombogenic drugs, angiogenic drugs, anti-angiogenic drugs, and thrombolytic agents.

25. The system of claim 22, wherein the active ingredient is a growth enhancer for encouraging cell growth.

26. The system of claim 25, wherein the growth enhancer is chosen from VEGF, alpha or beta FGF, platelet derived growth factors, autologous cells, and nucleic acid that encodes a therapeutic protein.

27. The system of claim 22, wherein the active ingredient is a radioactive material that emits radiation.

28. The system of claim 16, wherein the additive includes at least the imaging agent.

29. The system of claim 28, wherein the imaging agent is a pigment.

30. The system of claim 29, wherein the pigment is a water soluble dye.

31. The system of claim 28, wherein the imaging agent is radiopaque material.

32. The system of claim 31, wherein the radiopaque material is chosen from tantalum, tungsten, platinum, gold, barium sulfate, and titanium dioxide.

33. The system of claim 16, wherein the additive includes at least the bioadhesive agent for adhering the fiber to at least one of itself and body tissue.

34. The system of claim 33, wherein the bioadhesive is chosen from cyanoacrylate, chitosan, polylysine, polyethylene oxide, polypropylene oxide, cellulose derivatives, carboxy-methyl cellulose, polyethers, polysaccharides, mucopolysaccharides, hylauronic acid, fatty acid esters, Pluronics, polyacids cellulosic polymers, collagen, gelatin, poly HEMA, PVP, polymaleic anhydride, polyamide, polyacrylamide, polyvinylalcohol, and polyethylene glycol.

35. The system of claim 1, wherein the bulking agent is chosen from water soluble polymers and polymer solutions including blood compatible solvent water mixtures, alcohol water, and DMSO water solutions, and the reacting agent is chosen from ionic cross-linking agents, multi-valent ions, aldehyde cross-linkers, gluteraldehyde, divalent or trivalent ions, aziridine, D-glucono-gamma lactone, and isocyanates.

36. The system of claim 35, wherein the bulking agent is a water soluble polymer chosen from polyacids cellulosic polymers, chitosan, polylysine, collagen, gelatin, albumin, poly HEMA, PVP, polymaleic anhydride, polyamide, polyacrylic acid, heparin, sodium carboxymethyl cellulose, polyacrylamide, polyvinylalcohol, polyethylene glycol, polyethers, polyethylene oxide, functionalized polyethylene glycol derivatives, proteins, polysaccharide, and hydrogels.

37. The system of claim 35, wherein the reacting agent is a cross-linking agent chosen from calcium chloride, calcium gluconate, and calcium sulfate.

38. The system of claim 1, wherein the bulking agent includes alginate.

39. A system for delivering flowable substance capable of changing from liquid to solid for use as implants and surgical sealants, the system comprising:

a first reservoir containing a first flowable substance including a bulking agent;

a second reservoir containing a second flowable substance including a reacting agent; and a cannula including
a first lumen in fluid communication with the first flowable substance in the first reservoir, the first lumen including a first opening for allowing the first flowable substance to pass out of the cannula, and
a second lumen in fluid communication with the second flowable substance in the second reservoir, the second lumen including a second opening for allowing the second flowable substance to pass out of the cannula, wherein the cannula and the first and second flowable substances are configured so that the first and second flowable substances mix and form a fiber in a living being.

* * * * *

UNITED STATES PATENT AND TRADEMARK OFFICE
CERTIFICATE OF CORRECTION

PATENT NO.     : 6,629,947 B1  Page 1 of 1
DATED          : October 7, 2003
INVENTOR(S)    : Ronald A. Sahatijian et al.

It is certified that error appears in the above-identified patent and that said Letters Patent is hereby corrected as shown below:

<u>Column 11,</u>
Line 51, please replace "an" with -- a --.

<u>Column 13,</u>
Line 23, please replace "claim 13," with -- claim 23, --.

Signed and Sealed this

Thirteenth Day of January, 2004

JON W. DUDAS
*Acting Director of the United States Patent and Trademark Office*